(12) United States Patent
Hulse et al.

(10) Patent No.: US 9,485,986 B2
(45) Date of Patent: Nov. 8, 2016

(54) EVAPORATION OPERATIVE MATERIALS HAVING LOW ENVIRONMENTAL IMPACT

(75) Inventors: Ryan Hulse, Morristown, NJ (US); Diana Mercier, Morristown, NJ (US); Kane Cook, Morristown, NJ (US); Rajat S. Basu, Morristown, NJ (US); Martin R. Paonessa, Morristown, NJ (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 0 days.

(21) Appl. No.: 13/593,391

(22) Filed: Aug. 23, 2012

(65) Prior Publication Data

US 2013/0052354 A1 Feb. 28, 2013

Related U.S. Application Data

(60) Provisional application No. 61/526,859, filed on Aug. 24, 2011.

(51) Int. Cl.
*A01N 25/02* (2006.01)
*A01N 25/04* (2006.01)
*C10M 171/00* (2006.01)

(52) U.S. Cl.
CPC ............ *A01N 25/02* (2013.01); *A01N 25/04* (2013.01); *C10M 171/005* (2013.01); *C10M 2203/1006* (2013.01); *C10M 2229/025* (2013.01); *C10N 2250/04* (2013.01)

(58) Field of Classification Search
CPC ...... A01N 25/02; A01N 25/04; A01P 13/00; A01P 7/04; B05D 1/26; B05D 1/02; B05D 1/18; B05D 1/28; C01M 171/005; C01M 2203/1006; C01M 2229/025
USPC ........ 252/68, 67; 264/53; 427/384; 524/556, 524/588; 514/56, 772; 504/362
See application file for complete search history.

(56) References Cited

U.S. PATENT DOCUMENTS

| | | | | |
|---|---|---|---|---|
| 7,442,321 | B1 * | 10/2008 | Chen ..................... | C08J 9/144 252/67 |
| 2010/0102272 | A1 * | 4/2010 | Basu ..................... | C08J 9/127 252/182.12 |
| 2011/0041529 | A1 * | 2/2011 | Chen ..................... | C09K 5/044 62/115 |

FOREIGN PATENT DOCUMENTS

WO WO 2008121776 A1 * 10/2008 ............. C08J 9/146
WO WO 2010062572 A2 * 6/2010 ............. C08J 9/127

* cited by examiner

*Primary Examiner* — Michael M Bernshteyn
(74) *Attorney, Agent, or Firm* — Colleen D. Szuch

(57) ABSTRACT

A composition comprising: (a) at least one active component; and (b) a carrier in an amount effective to at least partially solvate or at least partially emulsify said active component, said carrier comprising monochloro,trifluoropropene.

10 Claims, No Drawings

EVAPORATION OPERATIVE MATERIALS HAVING LOW ENVIRONMENTAL IMPACT

CROSS REFERENCES TO RELATED APPLICATIONS

The present application claims priority to U.S. Provisional Application Ser. No. 61/526,859, filed on Aug. 24, 2011, the contents of which is incorporated herein by reference in its entirety.

FIELD OF THE INVENTION

This invention relates to compositions, methods and systems which include an active component and a solvent or carrier for the active component. As a result of the application of the composition in the intended manner, the active component becomes operative upon or in association with the removal, usually by evaporation, of the solvent or carrier.

BACKGROUND

Many applications involve the use of a material which acts as a carrier, dispersant, diluents, processing aid, and/or solvent for an active component or components. The carrier/dispersant/diluents/processing aid/solvent (hereinafter referred to sometimes as "carrier" for convenience) must be able to at least facilitate and preferably enhance the delivery and/or functioning of at least one of the active components at the location of intended use, and at the same time such carrier should not negatively interfere with the operation of the active components. Because the carrier will frequently in such situations be released into the open atmosphere upon use, the environmental properties of the carrier materials have become increasingly important as the concern about the environmental impact of man-made materials and activities has risen. For example, during the course of the past several years, substantial effort has been devoted to developing materials which have a much smaller impact on global warming and on depletion of the ozone layer in the field of refrigeration, for example. Furthermore, the release of materials into the atmosphere can have a negative impact on low-level atmospheric conditions, such as smog and haze.

In addition to favorable environmental properties, the material which is used for the carrier preferably also has a desirable but difficult to achieve combination of other properties, depending on the particular application, such as inertness with respect to the active ingredient(s), low toxicity and low flammability, among other properties. In many applications it is also either desirable or essential that the carrier have the ability to at least partially emulsify and/or to preferably at least partially solvate the active ingredient.

These and other needs are satisfied by preferred aspects of the present invention.

SUMMARY

The present invention provides compositions, methods and systems which comprise one or more active components and which utilize as a carrier a monochloro,trifluoropropene, and preferably 1-chloro-3,3,3-trifluoropropene ((HCFO-1233zd), and even more preferably trans-1-chloro-3,3,3-trifluoropropene (trans-HCFO-1233zd or HCFO-1233zd (E)) and/or cis-1-chloro-3,3,3-trifluoropropene (cis-HCFO-1233zd or HCFO-1233zd(Z)).

Applicants have unexpectedly found that the preferred compositions, methods and systems of the present invention provide not only highly favorable and desirable environmental properties, including preferably low GWP, low ODP and/or low VOC, the monochloro, trifluoropropene compounds described herein for use as the carrier possess a desirable but difficult to achieve mosaic of other properties, including substantial inertness with respect to the active ingredient(s), low toxicity and low flammability, among other properties. In many applications it is also either desirable or essential that the carrier have the ability to at least partially emulsify and/or to preferably at least partially solvate the active component. For many applications, including particularly coatings, paints, adhesives, sealant, lubricants (especially lubricants formed from fossil fuels or synthetic blends or versions thereof), and insecticide/herbicides, the ability of the carrier/active component combination to form an at least partially soluble and/or at least partially emulsifiable mixture can be highly desirable. Applicants have found that many preferred embodiments of the present invention provide a fluid composition in one or more of such applications which is at least partially soluble and/or partially emulsifiable mixture, and in even more preferred applications is substantially fully soluble and/or substantially fully emulsifiable. Furthermore, the compositions, methods and systems of the present invention have the advantage in many embodiments of providing the ability of the carrier to be readily removed with little or no additional steps after application of the material. Thus, in preferred compositions, methods and systems, the time required to cure/develop the active component is relatively low and requires relatively little, and preferably no additional energy after the application step.

In certain aspects of the present invention, the use of either the cis- or trans-HCFO-1233zd isomer is based on its solubility with the active agent. Applicants have surprisingly and unexpectedly discovered that the Kauri-Butanol (KB) number of cis-1233zd is 34 and that the KB number of trans-1233zd is 25. Thus, the cis-isomer has a KB number that is over 30% higher than the trans-isomer, suggesting that it, at least in certain application, may be a better solvent. Accordingly, and in certain aspects of the present invention, the monochloro,trifluoropropene selected, and in particular the HCFO-1233zd isomer selected, has a KB number of greater than 30. In further embodiment, the cis-HCFO-1233zd isomer may be specifically selected, alone or in conjunction with the trans-isomer, to provide a desired solubility to the active agent.

One preferred aspect of the present invention relates to adhesive compositions, methods and systems of bonding or preparing to bond two surfaces/bodies and adhesive systems which utilize an active component comprising a bonding agent and a carrier comprising a monochloro,trifluoropropene, and preferably HCFO-1233zd, and even more preferably trans-HCFO-1233zd or cis-HCFO-1233zd, wherein the bonding agent is capable of forming a bond between said at least two surfaces and/or bodies, upon delivery of the composition to the site of use, more preferably upon removal of, even more preferably upon evaporation of, at least a portion of the carrier. As used herein in connection with delivery, removal and evaporation, the term "upon" is intended to mean that those actions are at least part of or associated with, but not necessarily the exclusive means for, allowing the active component to achieve its desired result. As those skilled in the art will appreciate, the adhesive aspects of the present invention can find application in a wide variety of uses, including in connection with floor bonding, part fastening, building material bonding and the like.

Applicants have further discovered that cis- or trans-HCFO-1233zd may be specifically selected in adhesive applications depending upon its properties (e.g. flammability, Kauri-Butanol (KB) number, or the like), the method of application (e.g. sprayable or non-sprayable, etc.), and/or its solubility with the bonding agent used. By way of non-limiting example, in certain spray applications the trans-HCFO-1233zd isomer may be preferred because of its lower boiling point. In certain non-spray applications, the cis-HCFO-1233zd isomer may be preferred because it exhibits better solubility with the bonding agent. Alternatively, the trans-HCFO-1233zd isomer may be used alone, or in certain embodiments, in conjunction with one or more co-carriers (where necessary) to improve its solubility with the bonding agent.

To this end, and in certain aspects, the compositions of the present invention are provided as sprayable compositions, wherein the monochloro,trifluoropropene comprises, consists essentially of, or consists of trans-HCFO-1233zd. In further aspects, the compositions are non-sprayable compositions. In certain aspects, the monochloro,trifluoropropene of the non-sprayable compositions comprises, consists essentially of, or consists of cis-HCFO-1233zd. In even further aspects, the monochloro,trifluoropropene of the non-sprayable compositions comprises, consists essentially of, or consists of trans-HCFO-1233zd and at least one co-carrier, which improves solubility of trans-HCFO-1233zd with the active agent.

Another preferred aspect of the present invention relates to coating compositions, coating methods and coating systems which utilize an active component comprising a coating agent and a carrier comprising a monochloro,trifluoropropene, and preferably HCFO-1233zd, and even more preferably transHCFO-1233zd, wherein the coating agent is capable of forming a coating or film upon delivery of the composition to the site of use, more preferably upon removal of, even more preferably upon evaporation of, at least a portion of the carrier. As those skilled in the art will appreciate, the coating aspects of the present invention can find application in a wide variety of uses, including in connection with paints, thin films and the like. Applicants have further discovered that cis- or trans-HCFO-1233zd may be specifically selected in coating applications depending upon its properties (e.g. flammability, Kauri-Butanol (KB) number, or the like), the method of application (e.g. sprayable, non-sprayable, etc.), and/or its solubility with the coating agent used. By way of non-limiting example, in certain spray coating applications the trans-HCFO-1233zd isomer may be preferred because of its lower boiling point. In certain non-spray applications, the cis-HCFO-1233zd isomer may be preferred because it exhibits better solubility with the coating agent. Alternatively, the trans-HCFO-1233zd isomer may be used alone, or in certain embodiments, in conjunction with one or more co-carriers (where necessary) to improve its solubility with the coating agent.

Another preferred aspect of the present invention relates to sealant compositions, sealing methods and sealant systems which utilize an active component comprising a sealing agent and a carrier comprising a monochloro,trifluoropropene, and preferably HCFO-1233zd, and even more preferably trans-HCFO-1233zd or cis-HCFO-1233zd, wherein the sealing agent is capable of forming a seal or barrier particularly, though not exclusively, to the passage of sound, air, corrosive materials, or a pre selected fluid, such as moisture, upon delivery of the composition to the site of use, more preferably upon removal of, and even more preferably upon evaporation, of at least a portion of the carrier. As those skilled in the art will appreciate, the sealing aspects of the present invention can find application in a wide variety of uses, including in connection with vehicle body cavities, heavy equipment cavities, building cavities and the like. Applicants have further discovered that cis- or trans-HCFO-1233zd may be specifically selected in sealant applications depending upon its properties (e.g. flammability, Kauri-Butanol (KB) number, or the like), the method of its application, and/or its solubility with the sealing agent used. By way of non-limiting example, in certain spray applications the trans-HCFO-1233zd isomer may be preferred because it exhibits better solubility with the sealant agent. Alternatively, the trans-HCFO-1233zd isomer may be used alone, or in certain embodiments, in conjunction with one or more co-carriers (where necessary) to improve its solubility with the sealing agent.

Another preferred aspect of the present invention relates to lubricant compositions, lubricating methods and lubricating systems which utilize an active component comprising a lubricating agent and a carrier comprising a monochloro, trifluoropropene, and preferably HCFO-1233zd, and even more preferably trans-HCFO-1233zd or cis-HCFO-1233zd, wherein the lubricating agent is capable of providing or aiding in the reduction of friction between two surfaces or bodies upon delivery of the composition to the site of use, more preferably upon removal of, even more preferably upon evaporation, of at least a portion of the carrier. As those skilled in the art will appreciate, the lubricating aspects of the present invention can find application in a wide variety of uses, including in connection with bearings, fittings and the like. Applicants have further discovered that cis- or trans-HCFO-1233zd may be specifically selected depending upon its properties (e.g. flammability, Kauri-Butanol (KB) number, or the like), the method of its application, and/or its solubility with the lubricating agent used.

Another preferred aspect of the present invention relates to insecticidal and/or herbicidal compositions, methods of applying insecticide and/or herbicide, and to insecticidal and/or herbicidal systems which utilize an active component comprising an insecticidal agent and/or a herbicidal agent and a carrier comprising a monochloro, trifluoropropene, and preferably HCFO-1233zd, and even more preferably trans-HCFO-1233zd or cis-HCFO-1233zd, wherein the insecticide/herbicide agent is capable of inhibiting or enhancing the activity, growth and/or life of certain selected insect or plant life upon delivery of the composition to the site of use, more preferably upon removal, preferably upon evaporation, of at least a portion of the carrier. As those skilled in the art will appreciate, the insecticidal/herbicidal aspects of the present invention can find application in a wide variety of uses, including in connection with applications such as flying insect spays, weed killer sprays and the like. Applicants have further discovered that cis- or trans-HCFO-1233zd may be specifically selected depending upon its properties (e.g. flammability, Kauri-Butanol (KB) number, or the like), the method of its application, and/or its solubility with the insecticidal and/or herbicidal agent used.

As used herein the term "active component" refers to any one or more components of the composition which provide, contribute to and/or enhance the intended function of the composition, method or system. The term "carrier" is used herein generically to refer to any one or more components of the composition, system or method whose primary function is to provide a means for containing the active components, preferably in relatively dilute condition, and/or for aiding or contributing to the ease of application and/or effectiveness at the function of the location of intended use. Although the carrier component of the present invention generally does not act directly to form or produce the intended final product, it will be appreciated by those skilled in the art that the effectiveness of the carrier may nevertheless have an indirect impact on the properties of the final product by virtue of its effectiveness as a carrier, such as by evenly distributing the active component at the intended target location and/or leaving the active component in a more effective condition to perform its intended function.

DETAILED DESCRIPTION OF PREFERRED EMBODIMENTS

Although it is contemplated that the carrier of the present invention will comprise a major proportion of the composition, and in preferred embodiments the carrier will comprise from about 5% to about 95% of the composition, in further embodiments it comprises at least about 50% by weight, and even further embodiments at least about 80% by weight of a monochlorotrifluoropropene. It will be appreciated that other material may be included in the carrier in order to supplement or enhance the overall performance of the composition, method or system. The inclusion of any and all of such supplemental and additional materials in the carrier is within the broad scope of the present invention.

Examples of additional or supplemental materials that may be used in combination with the monchlorotrifluoropropene carrier component of the present invention include other hydrocarbons, other fluorocarbons, including other fluorochlorocarbons, fluoroethers, fluoroketones, alcohols, ketyones and/or formates. As mentioned above, these additional or supplemental components may be added, for example, to decrease the overall environmental impact and/or improve the performance of the composition, method or system.

In certain applications and embodiments, the carrier contributes to one or more of the following properties of the composition, method or system: flexibility of the material after removal of the carrier and curing or further processing of the active component; quality finish of the material after removal of the carrier and curing or further processing of the active component, quick dry times, and easy and/or effectiveness of application of the composition.

Coating Compositions, Methods and Systems

As mentioned above, the preferred coating compositions of the present invention comprise a coating agent and a carrier comprising a monochloro,trifluoropropene, and preferably HCFO-1233zd, and even more preferably trans-HCFO-1233zd and/or cis-HCFO-1233zd. The coating methods of the present invention comprise providing a coating composition according to the present invention and applying the coating composition to the substrate, body and/or surface to be coated. In certain embodiments, the methods comprise a further step which will aid, enhance or achieve removal of at least a substantial portion of the carrier from the substrate, body and/or surface so as to allow or enhance development of the desired coating by the coating agent. Although such further step may take many forms according to the present methods, in many applications such step simply comprises allowing the coating composition once applied to be exposed to the environment, which in many preferred embodiments will result in evaporation of at least a portion, and preferably a major proportion, and even more preferably substantially all of, the monotrifluoropropene. It will be appreciated that in some embodiments evaporation will be enhanced by heating of the coating composition once it is applied, which heating step may also provide additional benefits, for example by helping to accelerate development/curing of the coating and/or develop desirable properties in the coating once formed.

The coating agent can be a wide variety of materials and combinations according to the broad scope of the present invention. One embodiment of the coating aspects of the present invention comprises paints, painting methods and painting systems, or coating on one or more of a wide array of articles or devices. In the particular embodiment of paints, the active component can also take many forms and can comprise many materials. In certain preferred embodiments, the active component comprises an active resin that forms the paint coating when the carrier is at least partially removed and/or when the resin is cured. Although all known resins for this purpose can be used in accordance with the present invention, in certain embodiments the paint resin comprises a component such as oils, natural and/or synthetic polymers based on materials such as alkyds, acrylics, vinylacrylics, vinyl acetate/ethylene (VAE), polyurethanes, polyesters, melamine resins, epoxy, and combinations and mixtures of any two or more of these and/or other resin materials. In addition, the active component may comprise in addition to the resin one or more other materials such as aesthetic additives, pigments, binders and the like as is desired and/or needed to achieve the desired finish and other properties of the coating.

With respect to coating systems, it is contemplated although not generally preferred that the coating methods may require the application of two or more different compositions or material to achieve the desired final finish or coated surface. In such cases the systems of the present invention will comprise the present coating composition together with such additional materials or compositions which are intended to be or which are used together with the present coating compositions to achieve a coating according to the present invention.

As also noted above, for many coating applications, the selection of a particular HCFO-1233zd isomer may be based on its properties, the method of application and/or its solubility or miscibility with the coating agent. With certain spray applications, for example, the trans-HCFO-1233zd isomer may be preferred because it has a much lower boiling than the cis-isomer, but the cis-isomer may also be provided, as necessary, to assist with solubility of the coating agent. In such applications, the trans-isomer may be used with coating agents such as those provided above. In further non-limiting embodiments, the coating agents specifically may include acrylics, urethanes, styrene rubber, hydrocarbon rosin, ester rosin or heparin. In non-spray applications (e.g. dipping, pouring, brushing, immersing, etc.), it is particularly desirable that the carrier/active component combination form an at least partially soluble and/or at least partially emulsifiable mixture and that the selection of the isomer used may be based upon its solubility with the coating agent. In certain non-spray applications, the cis-HCFO-1233zd isomer is preferred because it exhibits better solubility with certain coating agents, particularly coating agents within the general categories provided above, and in further non-limiting and specific embodiments, high impact poly styrene, acrylonitrile-butadiene-styrene and some acrylics. Alternatively, in non-spray applications where the trans-HCFO-1233zd isomer may be preferred or otherwise used, it may be provided alone, or in certain embodiments, in conjunction with one or more co-carriers, particularly one or more co-carriers that improve solubility or miscibility of trans-1233zd with the coating agent. Examples of co-carriers in a coating application may include, but are not limited to, other hydrocarbons, other fluorocarbons, including other fluorochlorocarbons, fluoroethers, fluoroketones, alcohols, ketyones, formats, lower alcohols (such as methanol, ethanol, and the like), maphtha, terpene-based solvents, (such as d-limonene), other high evaporation rate organic materials (such as isoprene, hexane, heptane, styrene liquid, xylene, toluene, methylcyclohexane, cyclohexane. 2,2-dichloropropane, methylene chloride, diisobutyl ketone, diisopropylketone, methyl isobutyl ketone, methyl isopropyl ketone, methyl cyclohexanone, cyclohexanone, isobutyl acetate, isopropyl acetate, butyl acetate, propyl acetate, ethyl acetate, diethyl ether, dimethyl ether, diethylene glycol, 2-ethylhexanol) and mixtures of any of these with or without further materials used as co-carriers.

Applicants note that in the foregoing embodiments where one particular isomer may be preferred does not necessarily preclude the inclusion of the other or both isomers. Rather, it simply identifies qualities of one isomer that may be preferred for that application. Either isomer can be the provided in such applications alone, or otherwise in an isomeric mixture.

Adhesive Compositions, Bonding Methods and Adhesive Systems

As mentioned above, the preferred adhesive compositions of the present invention comprise a bonding agent and a carrier comprising a monochloro,trifluoropropene, and preferably HCFO-1233zd, and even more preferably trans-HCFO-1233zd and/or cis-HCFO-1233zd. The bonding methods of the present invention comprise providing a bonding composition according to the present invention and applying the bonding composition to at least one of the body(s) and/or surface(s) to be bonded. In most embodiments, the methods comprise bringing the bodies or surfaces together such that the bonding agent is able to effect a bond between the bodies/surfaces being adhered to one another. In some embodiments, the carrier or portion thereof is removed, preferably by evaporation, prior to the bodies/surfaces being brought together, while in other embodiments, the carrier or portion thereof is removed after the bodies/surfaces have been brought together. Of course embodiments may be used in which a portion of the carrier is removed before, during and after the bodies/surfaces are brought together.

Although it is not considered necessary for many embodiments, in certain embodiments it may be desirable to use a co-carrier in the adhesive aspects of the present invention. Such co-carrier may include, in addition to those mentioned above, lower alcohols (such as methanol, ethanol, and the like), terpene-based solvents, (such as d-limonene), other high evaporation rate organic materials (such as isoprene, hexane, heptane, styrene liquid, xylene, toluene, methylcyclohexane, cyclohexane. 2,2-dichloropropane, methylene chloride, diisobutyl ketone, diisopropylketone, methyl isobutyl ketone, methyl isopropyl ketone, methyl cyclohexanone, cyclohexanone, isobutyl acetate, isopropyl acetate, butyl acetate, propyl acetate, ethyl acetate, diethyl ether, dimethyl ether, diethylene glycol, 2-ethylhexanol) and mixtures of any of these with or without further materials used as co-carriers.

With respect to the method steps, the compositions of the present invention can be applied using a variety of techniques and steps, including but not limited to spraying, dipping, pouring, brushing, and combinations of these and other steps and techniques.

Other optional steps may be used to aid, enhance or achieve removal of at least a portion of the carrier from the composition and/or from the substrate, body and/or surface so as to allow or enhance development of the desired bond. Although such further steps may take many forms according to the present methods, in many applications such optional step comprises allowing the adhesive composition once applied to be exposed to the environment, which in many preferred embodiments will result in evaporation of at least a portion, and preferably a major proportion, and even more preferably of substantially all of, the monotrifluoropropene. It will be appreciated that in some embodiments evaporation will be enhanced by heating of the adhesive composition once it is applied, which heating step may also provide additional benefits, for example by helping to accelerate development/curing/reaction of the components of the bonding agent and/or develop desirable properties in the adhesive once the bond is formed.

The bonding agent can be a wide variety of materials and combinations according to the broad scope of the present invention. By way of non-limiting example, the active adhesive may be an acrylic adhesive, and epoxy adhesive, a styrenic adhesive, and combinations of these.

With respect to adhesive systems, it is contemplated although not necessarily preferred that the adhesive methods may require the application of two or more different compositions or materials to achieve the desired final bond. In such cases the systems of the present invention will comprise the present adhesive composition together with such additional materials or compositions which are intended to be or which are used together with the present adhesive compositions to achieve a bond according to the present invention.

As also noted above, for many adhesive applications, the selection of a particular HCFO-1233zd isomer may be based on its properties, the method of its application, and/or its solubility/miscibility with the bonding agent. With certain spray applications, for example, the trans-HCFO-1233zd isomer may be preferred because it has a much lower boiling than the cis-isomer, but the cis-isomer may also be provided, as necessary, to assist with solubility of the bonding agent. In such applications, the trans-isomer may be used with bonding agents, such as those within the general categories provided above. In certain aspect, the bonding agent specifically includes, but is not limited to, urethanes or styrene rubber. In non-spray applications, it is particularly desirable that the carrier/active component combination form an at least partially soluble and/or at least partially emulsifiable mixture and that the selection of the isomer used may be based upon its solubility with the bonding agent. In certain non-spray applications, the cis-HCFO-1233zd isomer may be preferred because it exhibits better solubility with the bonding agents, such as those within the general categories provided above, but particularly bonding agents that include, but are not limited to, acrylics, SBS or other styrenes, or the like. Alternatively, in alternative non-spray applications where the trans-HCFO-1233zd isomer may be preferred or otherwise used, it may be provided alone, or in certain embodiments, in conjunction with one or more of the co-carriers identified above, particularly a co-carrier that facilitates or otherwise improves solubility or emulsification of trans-1233zd with the bonding agent.

Applicants note that in the foregoing embodiments where one particular isomer may be preferred does not necessarily preclude the inclusion of both isomers. Rather, it simply identifies qualities of one isomer that are preferred for that application. Either isomer can be the provided in such applications alone, or otherwise in an isomeric mixture.

Sealant Compositions, Sealing Methods and Sealant Systems

As mentioned above, the preferred sealant compositions of the present invention comprise a sealing agent and a carrier comprising a monochloro,trifluoropropene, and preferably HCFO-1233zd, and even more preferably trans-HCFO-1233zd and/or cis-HCFO-1233zd. The sealing methods of the present invention preferably comprise providing a sealant composition according to the present invention and applying the sealant composition to at least one of the body(s) and/or surface(s) to be sealed. In many embodiments, the sealant is used to create a seal, and in certain embodiments a water seal, between two surfaces or bodies. In such embodiments, the methods preferably comprise bringing the bodies or surfaces together after the sealant has been applied to one or both bodies/surfaces such that the gap or space between them is relatively resistant to the flow of one or more fluids. In other embodiments, a gap exists or is created between the bodies/surfaces and the sealant is applied to the surfaces/bodies substantially simultaneously to fill and seal at least a portion of the gap. Additional embodiments include sound and air abatement and, the like. In either of such embodiments, pressure may be applied to the bodies and/or the sealant composition to improve the seal. In other embodiments, the sealant composition may be used to create in a relatively porous material, such as a fabric or the like, an increased resistance to the passage of one or more fluids, such as water, through the portion of the material which has been treated with the sealant of the present invention. In some embodiments, the carrier or portion thereof is removed, preferably by evaporation, prior to the bodies/surfaces being brought together, while in other embodiments, the carrier or portion thereof is removed after the bodies/surfaces have been brought together. Of course embodiments may be used in which a portion of the carrier is removed before, during and after the bodies/surfaces are brought together.

Other optional steps may be used to aid, enhance or achieve removal of at least a portion of the carrier from the composition and/or from the body and/or surface being treated so as to allow or enhance development of the desired seal. Although such further steps may take many forms according to the present methods, in many applications such optional step comprises allowing the sealant composition once applied to be exposed to the environment, which in many preferred embodiments will result in evaporation of at least a portion, and preferably a major proportion, and even more preferably of substantially all of, the monotrifluoropropene. It will be appreciated that in some embodiments evaporation will be enhanced by heating of the sealant composition once it is applied, which heating step may also provide additional benefits, for example by helping to accelerate development/curing/reaction of the components of the sealing agent and/or develop desirable properties in the sealant once the sealant is applied.

The sealing agent can be a wide variety of materials and combinations according to the broad scope of the present invention. By way of non-limiting example, the active sealing component may comprise one or more of silicone sealants, poly(alpha-monoalkenyl arene)/poly(conjugated diene) block copolymer or hydrogenated or partially hydrogenated derivatives thereof, and combinations of these with or without other active sealing agents.

With respect to adhesive systems, it is contemplated although not necessarily preferred that the sealant methods may require the application of two or more different compositions or materials to achieve the desired final bond. In such cases the systems of the present invention will comprise the present sealant composition together with such additional materials or compositions which are intended to be or which are used together with the present sealant compositions to achieve a seal according to the present invention.

As also noted above, for many sealant applications, the selection of a particular HCFO-1233zd isomer may be based on its properties, the method of application, and/or its solubility/miscibility with sealing agents. With certain spray applications, for example, the trans-HCFO-1233zd isomer may be preferred because it has a much lower boiling than the cis-isomer, but the cis-isomer may also be provided, as necessary, to assist with solubility of the sealing agent. In such applications, the trans-isomer may be used with sealing agents such as, but not limited to, those within the general categories provided above, but the cis-isomer may also be provided, as necessary, to assist with solubility of the sealing agent. In non-spray applications, it is particularly desirable that the carrier/active component combination form an at least partially soluble and/or at least partially emulsifiable mixture and that the selection of the isomer used may be based upon its solubility with the sealing agent. In certain non-spray applications, the cis-HCFO-1233zd isomer may be preferred because it exhibits better solubility with the sealing agents, such as, but not limited to, those within the general categories provided above. In alternative non-spray applications where the trans-HCFO-1233zd isomer may be preferred or otherwise used, it may be provided alone, or in certain embodiments, in conjunction with one or more co-carriers, particularly one or more co-carriers that improve solubility or emulsification of trans-1233zd with the sealing agent. Examples of co-carriers in a sealing application may include, but are not limited to, other hydrocarbons, other fluorocarbons, including other fluorochlorocarbons, fluoroethers, fluoroketones, alcohols, ketyones, formats, lower alcohols (such as methanol, ethanol, and the like), naphtha, terpene-based solvents, (such as d-limonene), other high evaporation rate organic materials (such as isoprene, hexane, heptane, styrene liquid, xylene, toluene, methylcyclohexane, cyclohexane. 2,2-dichloropropane, methylene chloride, diisobutyl ketone, diisopropylketone, methyl isobutyl ketone, methyl isopropyl ketone, methyl cyclohexanone, cyclohexanone, isobutyl acetate, isopropyl acetate, butyl acetate, propyl acetate, ethyl acetate, diethyl ether, dimethyl ether, diethylene glycol, 2-ethylhexanol) and mixtures of any of these with or without further materials used as co-carriers.

Applicants note that in the foregoing embodiments where one particular isomer may be preferred does not necessarily preclude the inclusion of both isomers. Rather, it simply identifies qualities of one isomer that are preferred for that application. Either isomer can be provided in such applications alone, or otherwise in a mixture of isomers.

Lubricant Compositions, Lubricating Methods and Lubricant Systems

As mentioned above, the preferred lubricant compositions of the present invention comprise a lubricating agent and a carrier comprising a monochloro,trifluoropropene, and preferably HCFO-1233zd, and even more preferably trans-HCFO-1233zd and/or cis-HCFO-1233zd. The lubricating methods of the present invention preferably comprise providing a lubricating composition according to the present invention and applying the lubricating composition to at least one of the body(s) and/or surface(s) to be lubricated. In many embodiments, the lubricant is used to create an area, region or surface of a body or material that exhibits a reduced level of friction when it comes in friction producing contact with another body. The selection of a particular HCFO-1233zd isomer may be based on its properties, the method of application, and/or its solubility/miscibility with lubricating agents. With certain spray applications, for example, the trans-HCFO-1233zd isomer may be preferred because it has a much lower boiling than the cis-isomer, but the cis-isomer may also be provided, as necessary, to assist with solubility of the lubricant. In non-spraying applications, cis- or trans-isomer may be used based, at least in part, on its solubility or miscibility with the lubricating agent. Applicants note, however, that the preference for one isomer does not necessarily preclude the inclusion of both isomers. Rather, it simply identifies qualities of one isomer that may be preferred for that application. Either isomer can be the provided in such applications alone, or otherwise in a mixture of isomers.

Various steps may be used to aid, enhance or achieve removal of at least a portion of the carrier from the composition and/or from the body and/or surface being treated so as to allow or enhance development of the desired lubricant. Although such further steps may take many forms according to the present methods, in many applications such optional step comprises allowing the lubricant composition once applied to be exposed to the environment, which in many preferred embodiments will result in evaporation of at least a portion, and preferably a major proportion, and even more preferably of substantially all of, the monotrifluoropropene. It will be appreciated that in some embodiments evaporation will be enhanced by heating of the lubricant composition once it is applied, which heating step may also provide additional benefits, for example by helping to accelerate development/curing/reaction of the components of the lubricanting agent and/or develop desirable properties in the lubricant once it is applied.

The lubricating agent can be a wide variety of materials and combinations according to the broad scope of the present invention. Commonly used active lubricating agents include but are not limited to Polyol Esters (POEs) and Poly Alkylene Glycols (PAGs), PAG oils, silicone oil, mineral oil, alkyl benzenes (ABs) and poly(alpha-olefin) (PAO). Commercially available mineral oils include Witco LP 250 (registered trademark) from Witco, Zerol 300 (registered trademark) from Shrieve Chemical, Sunisco 3GS from Witco, and Calumet R015 from Calumet. Commercially available alkyl benzene lubricants include Zerol 150 (registered trademark). Commercially available esters include neopentyl glycol dipelargonate, which is available as Emery 2917 (registered trademark) and Hatcol 2370 (registered trademark). Other useful esters include phosphate esters, dibasic acid esters, and fluoroesters. Of course, different mixtures of different types of lubricants may be used.

With respect to lubricant systems, it is contemplated although not necessarily preferred that the lubricating methods may require the application of two or more different compositions or materials to achieve the desired final lubricating effect. In such cases the systems of the present invention will comprise the present lubricant composition together with such additional materials or compositions which are intended to be or which are used together with the present lubricant compositions to achieve a friction reducing effect according to the present invention.

Insecticide Compositions, Insecticidal Methods and Insecticide Systems

As mentioned above, the preferred insecticide compositions of the present invention comprise a insecticidal agent and a carrier comprising a monochloro,trifluoropropene, and preferably HCFO-1233zd, and even more preferably trans-HCFO-1233zd and/or cis-HCFO-1233zd. The selection of a particular HCFO-1233zd isomer may be based on its properties, the method of application, and/or its solubility/miscibility with the insecticide. With certain spray applications, for example, the trans-HCFO-1233zd isomer may be preferred because it has a much lower boiling than the cis-isomer, but the cis-isomer may also be provided, as necessary, to assist with solubility of the insecticide. In non-spraying applications, cis- or trans-isomer may be used based, at least in part, on its solubility or miscibility with the insecticide. Applicants note, however, that the preference for one isomer does not necessarily preclude the inclusion of both isomers. Rather, it simply identifies qualities of one isomer that may be preferred for that application. Either isomer can be the provided in such applications alone, or otherwise in a mixture of isomers.

The insect reducing methods of the present invention preferably comprise providing an insecticidal composition according to the present invention and applying the insecticidal composition to at least one of the body(s), and/or surface(s), and/or the environment (including the air) to be treated. In many embodiments, the insecticide is used to create an area, region or surface of a body or material, or an area or region of the environment, that exhibits a relatively inhospitable condition to one or more insects and therefore reduces the presence or impact of such one or more insects on or near the region, body or the like.

Various steps may be used to aid, enhance or achieve removal of at least a portion of the carrier from the composition and/or from the body and/or surface and/or region of space being treated so as to allow or enhance development of the desired insecticide. Although such further steps may take many forms according to the present methods, in many applications such optional step comprises allowing the insecticide composition once applied to be exposed to the environment, which in many preferred embodiments will result in evaporation of at least a portion, and preferably a major proportion, and even more preferably of substantially all of, the monotrifluoropropene. It will be appreciated that in some embodiments other steps may be required to help or enhance the effectiveness of the active components of the insecticidal agent and/or develop desirable properties in the insecticide once the insecticide is applied.

The insecticidal agent can be a wide variety of materials and combinations according to the broad scope of the present invention. One embodiment of the insecticide aspects of the present invention comprises an improved insect spray, such as a wasp hornet or other flying insect spray. In such embodiments it is contemplated, and in some cases it is preferred that a propellant, preferably an environmentally friendly propellant such as HFO-1234ze, will be used to aid in spraying or expelling the present composition from the canister or can in which it may be stored prior to use. In such cases it is contemplated and preferred that the carrier component of the present invention preferably solvates, and even more preferably substantially completely solvates the active insecticidal components and thereby enhances the ability of the composition to penetrate into the body, surface, area or region to be treated, such as into a hornet or wasp nest, and to then relatively rapidly evaporate to allow the active ingredients to act effectively against the insects and to remain located in areas, regions or surfaces that would otherwise be difficult to treat with the insecticide.

By way of non-limiting example, active insecticides that may be used in accordance with the present invention comprise pyrethrins, piperonyl butoxide, and cabaryl. Optional additional ingredients may also be used, such as petroleum distillates and inert ingredients.

With respect to insecticide systems, it is contemplated although not necessarily preferred that the lubricating methods may require the application of two or more different compositions or materials to achieve the desired final insecticidal effect. In such cases the systems of the present invention will comprise the present insecticide composition together with such additional materials or compositions which are intended to be or which are used together with the present insecticide compositions to achieve the insecticidal effect according to the present invention.

Herbicide Compositions, Insecticidal Methods and Herbicide Systems

As mentioned above, the preferred herbicide compositions of the present invention comprise a herbicidal agent and a carrier comprising a monochloro, trifluoropropene, and preferably HCFO-1233zd, and even more preferably trans-HCFO-1233zd and/or cis-HCFO-1233zd. The selection of a particular HCFO-1233zd isomer may be based on its properties, the method of application, and/or its solubility/miscibility with herbicide. With certain spray applications, for example, the trans-HCFO-1233zd isomer may be preferred because it has a much lower boiling than the cis-isomer, but the cis-isomer may also be provided, as necessary, to assist with solubility of the herbicide. In non-spraying applications, cis- or trans-isomer may be used based, at least in part, on its solubility or miscibility with the herbicide. Applicants note, however, that the preference for one isomer does not necessarily preclude the inclusion of both isomers. Rather, it simply identifies qualities of one isomer that may be preferred for that application. Either isomer can be the provided in such applications alone, or otherwise in a mixture of isomers. The plant growth impacting methods of the present invention preferably comprise providing a herbicidal composition according to the present invention and applying the herbicidal composition to at least one of the body(s), and/or surface(s), and/or the environment (including the air) to be treated. In many embodiments, the herbicide is used to have positive or negative impact on the growth or health of one or more plants and therefore reduces or increases the presence or impact of such one or more plants on or near the region of treatment.

Various steps may be used to aid, enhance or achieve removal of at least a portion of the carrier from the composition and/or from the body and/or surface and/or region of space or ground being treated so as to allow or enhance development of the desired herbicide. Although such further steps may take many forms according to the present methods, in many applications such optional step comprises allowing the herbicide composition once applied to be exposed to the environment, which in many preferred embodiments will result in evaporation of at least a portion, and preferably a major proportion, and even more preferably of substantially all of, the monotrifluoropropene It will be appreciated that in some embodiments other steps may be required to help or enhance the effectiveness of the active components of the herbicidal agent and/or develop desirable properties in the herbicide once the herbicide is applied.

The herbicidal agent can be a wide variety of materials and combinations according to the broad scope of the present invention. One embodiment of the herbicide aspects of the present invention comprises an improved weed or plant spray. In such embodiments it is contemplated and in some cases preferred that a propellant, preferably an environmentally friendly propellant such as HFO-1234ze, will be used to help spray or expel the present composition form the canister or can in which it may be stored prior to use. In such cases it is contemplated and preferred that the carrier component of the present invention preferably solvates, and even more preferably substantially completely solvates the active herbicidal components and thereby enhances the ability of the composition to penetrate into the body, surface, area or region to be treated, and to then relatively rapidly evaporate to allow the active ingredients to act effectively to either enhance or inhibit growth of the selected plant matter and to remain located in areas, regions or surfaces that would otherwise be difficult to treat with the herbicide.

With respect to herbicide systems, it is contemplated although not necessarily preferred that the herbicidal methods may require the application of two or more different compositions or materials to achieve the desired final herbicidal effect. In such cases the systems of the present invention will comprise the present herbicide composition together with such additional materials or compositions which are intended to be or which are used together with the present herbicide compositions to achieve a growth/health regulating effect according to the present invention.

EXAMPLES

The following examples are provided for the purpose of illustrating the present invention but without limiting the scope thereof.

Example 1

Coating/Paint

The following active components comprising a coating agent, particularly a resin for use in paint, were tested in the indicated amounts and achieved the indicated results based on combining the carrier and the resin in 40 cc septum top vials and were shaken at room temperature (the Examples designated with a single letter suffix utilize trans-HFCO-1233zd and Examples designated with a double letter suffix utilize cis-HFCO-1233zd):

| Example | DOW* DESIGNATION | Description of Material | Grams of 1233zd(E)/1233zd(Z) | Grams of CoCarrier | Grams of Resin | Results |
|---|---|---|---|---|---|---|
| 1A | Paraloid ™ B-56 | Acrylic polymer | 9.89 | 0 | 0.47 | Complete dissolution |
| 1AA | Paraloid ™ B-56 | Acrylic polymer | 6.30 | 0 | 0.43 | Complete dissolution |
| 1B | Paraloid ™ B-66 | Acrylic polymer | 9.75 | 0 | 0.46 | Complete dissolution |
| 1BB | Paraloid ™ B-66 | Acrylic polymer | 6.13 | 0 | 0.45 | Complete dissolution |

-continued

| Example | DOW* DESIGNATION | Description of Material | Grams of 1233zd(E)/ 1233zd(Z) | Grams of CoCarrier | Grams of Resin | Results |
|---|---|---|---|---|---|---|
| 1C | Paraloid ™ B-67 | Acrylic polymer | 9.88 | 0 | 0.43 | Complete dissolution |
| 1CC | Paraloid ™ B-67 | Acrylic polymer | 6.08 | 0 | 0.45 | Complete dissolution |
| 1D | Paraloid ™ AU-608B | Acrylic polymer | 10.52 | 0 | 0.75 | milky, emulsion like liquid which phase separated |
| 1DD | Paraloid ™ AU-608B | Acrylic polymer | 4.59 | 0 | 0.51 | Complete dissolution |
| 1E | Paraloid ™ AU-608B | Acrylic polymer | 10.8 | 0.2 (methanol) | 0.87 | Complete dissolution, with no phase separation |

*All resins are manufactured by Dow Chemical Company and are identified herein by reference to the trade name, which may or may not be a registered trademark of Dow Chemical Company.

Example 2

Adhesive

The following active component comprising a bonding agent was tested in the indicated amounts and achieved the indicated results based on combining the carrier and the bonding agent in 40 cc septum top vials and were shaken at room temperature (the Examples designated with a single letter suffix utilize trans-HFCO-1233zd and Examples designated with a double letter suffix utilize cis-HFCO-1233zd):

| Example | 3M* DESIGNATION | Description of Material | Grams of 1233zd(E)/ 1233zd(Z) | Grams of CoCarrier | Grams of Resin | Results |
|---|---|---|---|---|---|---|
| 2A | Super 77 | Aerosol adhesive | 13.04 | 0 | 2.8 | A milky, emulsion like material was formed. This material phase separated |
| 2AA | Super 77 | Aerosol adhesive | 7.72 | 0 | 0.42 | A milky, emulsion like material was formed. This material phase separated |
| 2B | Super 77 | Aerosol adhesive | 11.57 | 0.23 | 0.46 | A milky, emulsion like material was formed. This material phase separated |
| 2BB | Super 77 | Aerosol adhesive | 7.48 | 0.15 | 0.35 | A milky, emulsion like material was formed. This material phase separated |

*The bonding agent is manufactured by 3M and is a aerosol adhesive identified herein by reference to the trade name, which may or may not be a registered trademark of 3M.

After the observed emulsion-like material designated as 2A in the table above was formed, the liquid was poured onto a metal surface, and substantially all of the carrier evaporated upon standing. The surface with the adhesive thereon became tacky, indicating the formation of a material ready to achieve bonding.

Example 3

Sealant

The following active component comprising a sealing agent was tested in the indicated amounts and achieved the indicated results based on combining the carrier and the sealing agent in 40 cc septum top vials and were shaken at room temperature (the Examples designated with a single letter suffix utilize trans-HFCO-1233zd and Examples designated with a double letter suffix utilize cis-HFCO-1233zd):

| Example | DAP* DESIGNATION | Description of Material | Grams of 1233zd(E)/ 1233zd(Z) | Grams of CoCarrier | Grams of Resin | Results |
|---|---|---|---|---|---|---|
| 3A | Dap Silicone Caulk (clear) | Silicone Caulk (clear) | 14.09 | 0 | 0.77 | A milky, emulsion like material was formed. This |

-continued

| Example | DAP* DESIGNATION | Description of Material | Grams of 1233zd(E)/ 1233zd(Z) | Grams of CoCarrier | Grams of Resin | Results |
|---------|------------------|-------------------------|-------------------------------|--------------------|----------------|---------|
| 3AA | Dap Silicone Caulk (clear) | Silicone Caulk (clear) | 12.15 | 0 | 0.82 | material phase separated A milky, emulsion like material was formed. This material phase separated |
| 3B | Super 77 | Aerosol adhesive | 5.49 | 0.11 | 5.34 | A single phase id formed (complete dissolution) with no phase separation |

*The sealing agent is manufactured by DAP and is a silicon caulk identified herein by reference to the trade designation Dap Silicone Caulk (clear), which may or may not be a registered trademark of DAP.

Example 4

Lubricant

A carrier consisting of 1234ze(E) according to the present invention is combined with mineral oil in a relative amount which is effect to allow the carrier to carry and substantially dissolve or emulsify, or a combination thereof, the mineral oil. The mineral oil is present in an amount effective to provide lubrication upon application to a surface. In particular, the following active component comprising a lubricant in the form of mineral oil is tested in the indicated amounts and achieved the indicated results based on combining the carrier and the lubricant in 40 cc septum top vials and were shaken at room temperature (the Examples designated with a single letter suffix utilize trans-HFCO-1233zd and Examples designated with a double letter suffix utilize cis-HFCO-1233zd):

| Example | Lubricant DESIGNATION | Description of Material | Grams of 1233zd(E)/ 1233zd(Z) | Grams of CoCarrier | Grams of oil | Results |
|---------|----------------------|-------------------------|-------------------------------|--------------------|--------------| --------|
| 4A | WITCO LP 150 | Mineral Oil | 10 | 0 | 10 | Complete dissolution |
| 4AA | WITCO LP 150 | Mineral Oil | 10 | 0 | 10 | Complete dissolution |
| 4B | DOW Corning 360 Silicone | Silicone Lubricant | 10 | 0 | 10 | Complete dissolution |
| 4BB | DOW Corning 360 Silicone | Silicone Lubricant | 10 | 0 | 10 | Complete dissolution |

Example 5

Insecticide

Carriers consisting of 1233zd(E) and 1233zd(Z) according to the present invention is combined with an insecticidal material having typical insecticidal properties in a relative amount according to the teachings contained herein and which is an amount is effect to allow the carrier to carry and substantially dissolve or emulsify, or a combination thereof, the insecticide. The insecticide is present in an amount effective to provide an insecticidal effect upon application using typical application techniques.

Example 6

Herbicide

Carriers consisting of 1233zd(E) and 1233zd(Z) according to the present invention is combined with an insecticidal material having typical insecticidal properties in a relative amount according to the teachings contained herein and which is effect to allow the carrier to carry and substantially dissolve or emulsify, or a combination thereof, the herbicide. The herbicide is present in an amount effective to provide an insecticidal effect upon application using typical application techniques.

Example 7

Measurement of Kauri-Butanol Number

Measurement of Kauri-Butanol (KB) number was performed in the lab for both tr-1233zd and cis-1233zd using the ASTM method (D1133 Standard Test Method for Kauri-Butanol Value of Hydrocarbon Solvents). Kauri-Butanol number of a solvent is a measure of how well Kauri-gum resin solution is dissolved in a solvent and is used widely in industry to compare solvency of compounds. Kauri-butanol solution was obtained from Fisher Scientific. Both tr-1233zd & cis-1233zd were titrated in to the solution which were kept in a 20 cc vial with septum screw cap. KB number for tr-1233zd was found to be 25 and KB number for cis-1233zd was found to be 34. Unexpectedly the KB value of cis-1233zd increased by >30% over the KB value of the tr-1233zd. CFC-113 which was a widely used solvent in a variety of cleaning applications including but not limited to electronics cleaning, dry cleaning, metal cleaning and deposition had a KB value of 31. Cis-1233zd would be a preferred solvent due to its higher KB value when looking at electronics cleaning, dry cleaning, metal cleaning and deposition.

Example 8

Solubility of Acrylic

Test samples of commercial acrylic plastic sheet cut into ¼"×2" piece were placed into 20 cc vials with septum screw cap. Solvents (tr-1233zd & cis-1233zd) were slowly added by a syringe to cover the entire plastic sample inside the vial. The purpose was to observe if any degradation happens to the plastic. Acrylic materials were found to dissolve acrylic material readily in both solvents.

Example 9

Solubility of High Impact Styrene

Test samples of commercial high impact styrene plastic sheet cut into ¼"×2" piece were placed into 20 cc vials with septum screw cap. Solvents (tr-1233zd & cis-1233zd) were slowly added by a syringe to cover the entire plastic sample inside the vial. The purpose was to observe if any degradation happens to the plastic. High impact styrene materials were found to dissolve completely in cis-1233zd solvent whereas it only showed swelling in tr-1233zd solvent. This shows distinct uniqueness in solubility of cis-1233zd over tr-1233zd.

Example 10

Solubility of Acrylonitrile-Butadiene-Styrene

Test samples of commercial acrylonitrile-butadiene-styrene (ABS) sheet cut into ¼"×2" piece were placed into 20 cc vials with septum screw cap. Solvents (tr-1233zd & cis-1233zd) were slowly added by a syringe to cover the entire plastic sample inside the vial. ABS plastic materials were found to dissolve completely in cis-1233zd solvent whereas it only showed deformations in tr-1233zd solvent. This also demonstrates distinct uniqueness in solubility of cis-1233zd over tr-1233zd.

Example 11

Solubility of Polycarbonate

The experiment in Example 8 is repeated with commercial polycarbonate material. Tr-1233zd has some minor effect on polycarbonate in that the polycarbonate was seen to be crazed but cis-1233zd had significant effect in that the polycarbonate had severe crazing and even cracks after exposure to cis-1233zd.

Example 12

Solubility of Acrylic

The experiment of Example 8 was repeated with commercial Dow Polaroid™ Au-608-B acrylic material. This material is used in various coatings. Tr-1233zd cannot dissolve the material without any co-solvent added but cis-1233zd dissolved it completely.

Example 13

Solubility of Heparin

The experiment of Example 8 was repeated with blood anti-coagulant material Heparin, which is used as a coating in medical devices. Heparin is effective at preventing deep vein thromboses and pulmonary emboli in patients at risk. None of the solvents could dissolve the material. When 2 wt % methanol is added to each of the material the solution of tr-1233zd and methanol could dissolve 0.794 wt % heparin and cis-1233zd and methanol could dissolve 1.19 wt % heparin and remained clear being left overnight.

What is claimed is:

1. An evaporation operative acrylic coating composition comprising:
   (a) at least one active component comprising at least one acrylic resin, said active component being capable of forming an acrylic coating or film; and
   (b) a carrier solvating and/or emulsifying said active component, said carrier comprising at least 5% by weight of 1-chloro-3,3,3-trifluoropropene, wherein said 1-chloro-3,3,3-trifluoropropene present in the carrier consists essentially of trans-1-chloro-3,3,3-trifluoropropene (HFO-1233zd(E)), whereby said active component becomes operative upon evaporation of said carrier from said coating composition to form an acrylic coating.

2. The coating composition of claim 1 wherein said 1-chloro-3,3,3-trifluoropropene consists of trans-1-chloro-3,3,3-trifluoropropene (trans-HCFO-1233zd).

3. A sprayable coating composition comprising the coating composition of claim 1.

4. The sprayable coating composition of claim 3 wherein said 1-chloro-3,3,3-trifluoropropene consists of trans-1-chloro-3,3,3-trifluoropropene (trans-HCFO-1233zd).

5. The coating composition of claim 1 wherein said carrier has a KB value of greater than 30.

6. The coating composition of claim 5 wherein the 1-chloro-3,3,3-trifluoropropene consists of trans-1-chloro-3,3,3-trifluoropropene (trans-HCFO-1233zd.

7. The coating composition of claim 1, further comprising at least one co-carrier selected from the group consisting of a lower alcohol, a terpene-based solvent, a high evaporation rate organic material, and combinations thereof.

8. The coating composition of claim 7, wherein the co-carrier is selected from the group consisting of methanol, ethanol, d-limonene, isoprene, hexane, heptane, styrene liquid, xylene, toluene, methylcyclohexane, cyclohexane, 2-2-dichloropropane, methylene chloride, diisobutyl ketone, diisopropylketone, methyl isobutyl ketone, methyl isopropyl ketone, methyl cyclohexanone, cyclohexanone, isobutyl acetate, isopropyl acetate, butyl acetate, propyl acetate, ethyl acetate, diethyl ether, dimethyl ether, diethylene glycol, 2-ethylhexanol, and combinations thereof.

9. The coating composition of claim 1 wherein said carrier does not interfere with the formation of a coating comprising said active component.

10. The coating composition of claim 9 wherein said carrier does not interfere with the formation of an acrylic coating.

* * * * *